United States Patent [19]

Elger et al.

[11] Patent Number: 4,888,331
[45] Date of Patent: Dec. 19, 1989

[54] COADMINISTRATION OF ANTIGESTAGEN AND ANTIESTROGEN FOR GYNECOLOGICAL DISORDERS, ABORTION AND LABOR INDUCTION

[75] Inventors: Walter Elger; Sybille Beier; Marianne Fähnrich; Beate Kosub; Krzysztof Chwalisz; Syed H. Hasan, all of Berlin, Fed. Rep. of Germany

[73] Assignee: Schering Aktiengesellschaft, Berlin and Bergkamen, Fed. Rep. of Germany

[21] Appl. No.: 252,299

[22] Filed: Oct. 3, 1988

[30] Foreign Application Priority Data

Oct. 1, 1987 [DE] Fed. Rep. of Germany ....... 3733478

[51] Int. Cl.$^4$ .............................................. A61K 31/56

[52] U.S. Cl. .................................... 514/170; 514/171
[58] Field of Search ................................ 514/170, 171

[56] References Cited

U.S. PATENT DOCUMENTS 4,670,426 6/1987 Zor et al. ............................ 514/171

Primary Examiner—Douglas W. Robinson
Assistant Examiner—Joseph A. Lipovsky
Attorney, Agent, or Firm—Millen, White & Zelano

[57] ABSTRACT

An agent containing at least one compound having antiprogestational activity and at least one compound having anti-estrogenic activity is disclosed. The agent is suitable for the induction of labor, termination of pregnancy, as well as for the treatment of gynecological disorders.

19 Claims, 1 Drawing Sheet

COADMINISTRATION OF ANTIGESTAGEN AND ANTIESTROGEN FOR GYNECOLOGICAL DISORDERS, ABORTION AND LABOR INDUCTION

BACKGROUND OF THE INVENTION

The invention relates to agents containing at least one compound having antiprogestational activity (AG) and at least one compound having anti-estrogenic activity (AE). The invention concerns, in particular, agents of the indicated type for induction of labor and for termination of pregnancy, as well as for the treatment of gynecological disorders. The invention also relates to the use of a combination of AG with AE for the above-mentioned indications.

In order to avert danger to mother and/or child, it is sometimes necessary to induce labor artificially or to terminate a pregnancy prematurely. For this purpose, surgical techniques and pharmacological methods are available.

A possible pharmacological method is vaginal or intramuscular administration of prostaglandins which is used in case of terminating a pregnancy in the first or second trimester of pregnancy (Contraception 1983, 27 : 51–60 and Int. J. Gynaecol. Obstet. 1982, 20 : 383–386).

The advantage inherent in using prostaglandins is the possibility of utilizing them over a long time period of pregnancy. Disadvantages of the prostaglandins are acute side effects, such as pain and nausea. Besides, the success rate in case of termination of pregnancy in advanced stages of pregnancy is no more than 90% even with a prolonged duration of prostaglandin treatment.

Another possibility of terminating pregnancy resides in the administration of an antigestagen (Med. et Hyg. 1982, 40 : 2087–2093). Antigestagens are more compatible than prostaglandins, but they have lower efficacy, higher latency and individual variability of onset of activity as compared with the prostaglandins. Besides, it has been observed in the clinic that they exhibit tendency toward, in part, severe hemorrhages.

The combined use of prostaglandins and antigestagens (U.S. Pat. No. 4,626,531, issued on Dec. 2, 1986), although affording irrefutable advantages over the sole administration of the individual active agents (above all, reduction of the respective quantity of active ingredient), does not solve the problems, for example, which occur generally with the use of prostaglandins. These problems include undesirable side effects, such as gastrointestinal effects or pain in the uterus. In addition, treatment must take place on an inpatient basis; moreover, storage and shelf life of the drug are limited and/or expensive because of their lack of stability; and the most user-friendly form of administration, namely oral, is impossible. Thus,-it is likewise impossible to combine both active agents in a tablet, pill, or dragee.

Pharmaceutical compositions for postcoital fertility control, containing a competitive progesterone antagonist (antigestagen) as well as a progesterone and estrogen synthesis blocker, have been described in U.S. Pat. No. 4,670,426. Typical representatives for the competitive progesterone antagonist to be used which are mentioned are fluocinolone acetonide, triamcinolone acetonide, steroids having a cyclic 16, 17-acetal with acetone and 17$\beta$-hydroxy-11$\beta$-(4-dimethylaminophenyl-1)-17$\alpha$-prop-1-ynyl)estra-4, 9-dien-3-one, and equivalent derivatives. The typical content ranges between 20 and 50 mg. Examples cited for the progesterone and estrogen synthesis blocker are aminoglutethimide, 2$\alpha$-cyano-4, 4, 117$\alpha$-trimethyl-5-androst-5-en-17$\beta$-ol-3-one, 20, 25-diazocholesterol, and compounds having equivalent activity, namely in a dosage of 300–1,000 mg. The use of the composition, according to U.S. Pat. No. 4,670,426 must take place maximally early within the first week after sexual intercourse over a time period of 3 days; most advantageously, treatment should be continued for 2–6 days. The prevention of nidation and thus pregnancy is brought about by the synergistic effect in the combined use of the two components of the composition, namely with a success rate on the order of magnitude of 90% or thereabove. See also commonly assigned U.S. Ser. No. 206,750 of Jun. 15, 1988.

For induction of labor, termination of pregnancy, and treatment of gynecological disorders, compounds having anti-estrogenic activity have not been proposed heretofore.

SUMMARY OF THE INVENTION

This invention provides compositions useful as pharmaceuticals, e.g., medicinal agents useful for the above-mentioned usages which do not exhibit the aforementioned disadvantages, simultaneously show a high efficacy, if possible a higher efficacy as compared with the conventional agents, and have fewer side effects as compared to conventional agents.

Upon further study of the specification and appended claims, further objects and advantages of this invention will become apparent to those skilled in the art.

This invention provides a combination of AG and AE, whereby the efficacy of the individual components is surprisingly dramatically enhanced. The AE component alone is not effective for termination of pregnancy.

The combination according to the invention is not only suitable to a high degree for induction of labor and for termination of pregnancy; the combination even finds additional use as an agent against gynecological disorders such as endometriosis and dysmenorrhea. Other utilities for the combination including the treatment of hormone dependent tumors are discussed in co-pending application Ser. No. 252,612, filed on even date. It is demonstrated for the first time that the effects of AG and AE mutually enhance each other by virtue of the agents of this invention.

The weight ratio of both components can herein be varied within wide limits for the treatment of the above-mentioned indications in a patient, e.g., mammals, including humans. Thus, it is possible to employ the same amounts of AG and AE as well as also an excess of one of the two components. AG and AE are utilized jointly, separately, simultaneously and/or staggered chronologically (sequentially), in a weight ratio of about 1:50 to 50:1, preferably 1:25 to 25:1, and especially 1:10 to 10:1. The simultaneous administration is preferred. In case of sequential administration, the compound administered as the second one can be given at any time after administration of the first-administered compound, as long as it becomes bio-available in the female patient simultaneously with an effective amount of the first-administered compound. For example, AE can be given starting with the 2nd day after administration of AG, it being possible to administer, on the 3rd and 4th days, additionally also AG as well as AE.

The combined treatment with AG and AE for terminating pregnancy takes place normally over 1 to 4, preferably 1 to 2 days. In accordance with the present invention, for terminating gravidity and for induction of labor, the combination of AG and AE is administered in any event after nidation, preferably in the second or third trimester of gravidity, and in case of induction of labor shortly before or one the date of birth.

Preferably, AG and AE are administered combined in one dosage unit.

Suitable antigestagens include all compounds showing strong affinity to the gestagen receptor (progesterone receptor) while not exhibiting any progestational activity on their own. Examples of suitable but not limiting competitive progesterone antagonists are the following steroids: 11β-[(4-N, N-dimethylamino)-phenyl]-17β-hydroxy-17α-propynyl-4, 9(10)-estradien-3-one (RU-38486, EP-A 0 057 115), 11β-[(4-N,N-dimethylamino)phenyl]-17β-hydroxy-18-methyl-17αpropynyl-4,9(10)-estradien-3-one, and 11β-[(4-N,N-dimethylamino)phenyl]-17aβ-hydroxy-17αpropynyl-D-homo-4, 9(10),16-estratrien-3-one (EP-A 0 057 115); 11β-p-methoxyphenyl-17β-hydroxy-17αethynyl-4,9(10)-estradien-3-one [Steroids 37 : 361-382 (1981)]and 11β-(4-dimethylaminophenyl-17αhydroxy-17β-(3-hydroxy-propyl)-13αmethyl-4,9-gonadien-3-one (EP-A 0 129 499); or mixtures of the above-mentioned AG agents.

The antigestagens can be utilized in accordance with this invention for the termination of pregnancy in a patient, e.g., mammals (the customary antigestagens alone are frequently not adequate for a 100% success rate). In general, 10–200 mg of 11β-[(4-N,N-dimethylamino)-phenyl]-17α-hydroxy-17β-(3-hydroxypropyl)-13α-methyl-4,9(10)-gonadien-3-one per day, or a biologically equivalent amount of another antigestagen, will be sufficient.

The dosage in the treatment of gynecological disorders is 1–1,000 mg, preferably 10 to 200 mg, of 11β[(4 N,N-dimethylamino)-phenyl]-17α-hydroxy-17β-(3-hydroxypropyl)-13α-methyl-4,9(10)-gonadien-3-one per day or a biologically equivalent amount of another antigestagen.

Suitable compounds having anti-estrogenic activity are anti-estrogens and aromatase inhibitors, or mixtures thereof. Anti-estrogens and aromatase inhibitors in accordance with the present invention can either be derived from steroids or they can be nonsteroidal compounds. The anti-estrogens act as competitive estrogen antagonists in that they displace estrogen from the receptor whereas aromatase inhibitors suppress the biosynthesis of estrogen. Compounds such as the aminoglutethimides used in USP 4,670,426, i.e., 3-(4-aminophenyl)piperidine-2, 6-diones alkylated in the 3-position and others, which have a lowering effect on other sexual hormone serum concentrations (e.g., progesterone) as well as in the estrogen level, are unsuitable according to this invention as compounds having anti-estrogen activity. Thus, compounds having anti-estrogenic activity in accordance with the present invention are understood to include those compounds having a maximally selective effect in this sense, i.e., excluding those which also inhibit the effect of sexual hormones other than estrogens and/or lower their concentration.

All of the conventional anti-estrogens of this nature are suitable as the anti-estrogens. They can be utilized in approximately the same amounts as the antiestrogens already available commercially, i.e., the daily dosage is about 5–100 mg for tamoxifen or biologically equivalent amounts of another anti-estrogen. Examples of nonsteroidal anti-estrogens are:

tamoxifen (Z)-2-[p-(1, 2-diphenyl-1-butenyl)phenoxy]-N,N-dimethylethylamine, nafoxidine = 1-[2-[4-(6-methoxy-2-phenyl-3,4-dihydro-1-naphthyl)phenoxy]ethyl]pyrrolidine hydro chloride, and Mer 25  1-[p-(2-diethylaminoethoxy)phenyl]-2-(p-methoxyphenyl)-1-phenylethanol.

Examples of suitable steroidal anti-estrogens are, e.g., 11α-methoxy-17α-ethynyl-1, 3, 5(10)-estratriene -3, 17β-diol, and 16β-ethylestradiol.

Mixtures of the above-mentioned anti-estrogens can be used.

Suitable aromatase inhibitors are all compounds suitable as a substrate for aromatase, such as, for example, 1-methylandrosta-1, 4-diene-3, 17-dione, described in German Laid-Open Application 3,322,285;

testolactone (17a-oxa-D-homoandrosta-1,4-diene-3, 17-dione) disclosed in "Journal of Clinical Endocrinology and Metabolism"49 : 672 (1979);

the compounds described in "Endocrinology" 1973, vol. 92, No. 3, page 874: androsta-4,6-diene-3,17-dione, androsta-4,6-dien-17β-ol-3-one acetate, androsta-1,4,6-triene-3,17-dione, 4-androstene-19-chloro-3,17-dione, 4-androstene-3, 6, 17-trione;

the 19-alkynylated steroids disclosed in German Laid-Open Application 3,124,780;

the 10-(1,2-propadienyl) steroids described in German Laid-Open Application 3,124,719;

the 19-thioandrostane derivatives set forth in European Patent Application, Publication No. 100 566;

4-androsten-4-ol-3,17-dione, disclosed in "Endocrinology" 1977, vol. 100, No. 6, page 1684 and in U.S. Pat. No. 4,235,893, and its esters;

the 1-methyl-15αalkyl-androsta-1,4-diene-3,17-diones described in German Laid-Open Application 3,539,244;

the 10β-alkynyl-4,9(11)-estradiene derivatives described in German Laid-Open Application 3,644,358; and 1,2β-methylene-6-methylene-4-androstene-3,17-dione disclosed in European Patent Application 0 250 262; or mixtures thereof.

An example of a non-steroidal aromatase inhibitor is [4-(5,6,7,8-tetrahydroimidazo[1,5αpyridin-5-yl)benzonitrile monohydrochloride](Cancer Res. 48 : 834–838, 1988).

In general, 10–200 mg daily of 1-methyl-androsta1,4-diene-3,17-dione or biologically equivalent doses of other aromatase inhibitors are utilized for induction of labor or termination of pregnancy in a patient, e.g., mammals.

Dosage ranges for the treatment of gynecological disorders is 1–1000 mg, preferably 5–50 mg, of 1-methylandrosta-1,4-diene-3, 17-dione per day, or biologically equivalent doses of other aromatase inhibitors.

The compounds having antiprogestational and antiestrogenic activities can be, for example, applied locally or topically, or administered enterally or parenterally.

Especially suitable for enteral administration, which is preferred, are tablets, dragees, capsules, pills, suspensions, or solutions; these can be prepared in the usual way with the additives and excipients customary in galenic pharmacy. Suitable for local or topical application are, for example, vaginal suppositories or transdermal systems, such as skin plasters.

One AG dosage unit can contain about 1–200 mg of 11β-[(4-N,N-dimethylamino)phenyl]-17α-hydroxy-17β-(3-hydroxypropyl)-13α-methyl-4,9(10)-gonadien- 3-one or a biologically equivalent amount of another antigestagen.

One AE dosage unit can contain 1–100 mg of tamoxifen or 10–200 mg of 1-methylandrosta-1,4-diene-3,17-dione or a biologically equivalent quantity of another compound having anti-estrogenic activity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

BRIEF DESCRIPTION OF THE DRAWING

Various other objects, features and attendant advantages of the present invention will be more fully appreciated as the same becomes better understood when considered in conjunction with the accompanying drawing in which like reference characters designate the same or similar parts throughout the several views, and wherein.

Figure 1:
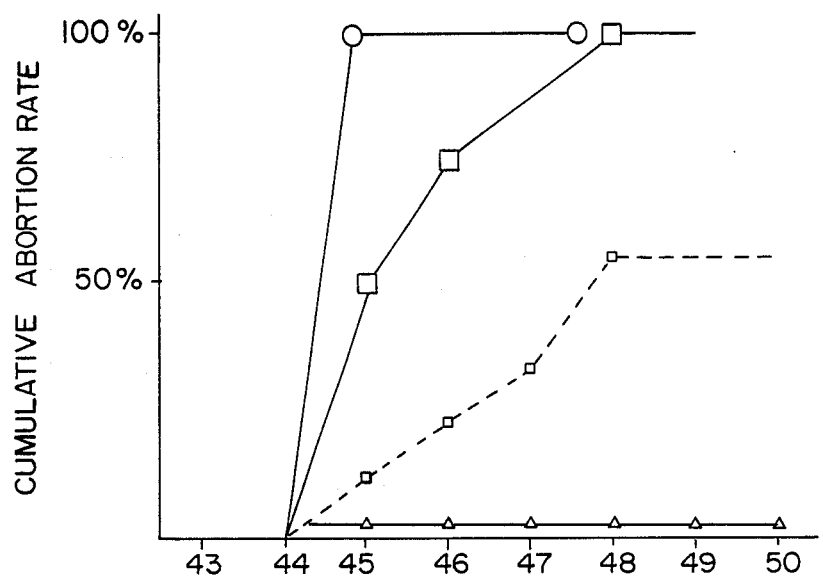
FIG. 1 depicts the comparative study of abortive effect of compounds having antiprogestational and antiestrogenic activities in gravid guinea pigs.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 37 33 478.6 (the priority document), are hereby incorporated by reference.

EXAMPLE 1

| | |
|---|---|
| 10.0 mg | 11β-[(4-N,N—Dimethylamino)phenyl]-17α-hydroxy-17β-(3-hydroxypropyl)-13α-methyl-4,9-gonadien-3-one |
| 140.5 mg | Lactose |
| 69.5 mg | Cornstarch |
| 2.5 mg | Polyvinylpyrrolidone 25 |
| 2.0 mg | "Aerosil" |
| 0.5 mg | Magnesium stearate |
| 225.0 mg | Total weight of tablet |

EXAMPLE 2

| | |
|---|---|
| 50.0 mg | 1-Methylandrosta-1,4-diene-3,17-dione |
| 115.0 mg | Lactose |
| 50.0 mg | Cornstarch |
| 2.5 mg | Poly-N—vinylpyrrolidone 25 |
| 2.0 mg | "Aerosil" |
| 0.5 mg | Magnesium stearate |
| 220.0 mg | Total weight of tablet |

EXAMPLE 3

| | |
|---|---|
| 25.0 mg | 1-Methylandrosta-1,4-diene-3,17-dione |
| 25.0 mg | 11β-[(4-N,N—Dimethylamino)phenyl]-17α-hydroxy-17β-(3-hydroxypropyl)-13α-methyl-4,9-gonadien-3-one |
| 115.0 mg | Lactose |
| 50.0 mg | Cornstarch |
| 2.5 mg | Poly-N—vinylpyrrolidone 25 |
| 2.0 mg | "Aerosil" |
| 0.5 mg | Magnesium stearate |
| 220.0 mg | Total weight of tablet which is manufactured in the usual way on a tabletting press. If desired, the active ingredients according to this invention can also be pressed, with respectively one-half of the above-indicated additives, separately into a two-layer tablet. |

EXAMPLE 4

| | |
|---|---|
| 10.0 mg | Tamoxifen |
| 10.0 mg | 11β-[(4-N,N—Dimethylamino)phenyl]-17α-hydroxy-17β-(3-hydroxypropyl)-13α-methyl-4,9-gonadien-3-one |
| 135.0 mg | Lactose |
| 60.0 mg | Cornstarch |
| 2.5 mg | Poly-N—vinylpyrrolidone 25 |
| 2.0 mg | "Aerosil" |
| 0.5 mg | Magnesium stearate |
| 220.0 mg | Total weight of tablet which is manufactured in the usual way on a tabletting press. If desired, the active ingredients according to this invention can also be pressed, with respectively one-half of the above-cited additives, separately into a two-layer tablet. |

EXAMPLE 5

Composition of an Oily Solution

| | |
|---|---|
| 100.0 mg | Tamoxifen |
| 343.4 mg | Castor oil |
| 608.6 mg | Benzyl benzoate |
| 1,052.0 mg | = 1 ml |

EXAMPLE 6

Composition of an Oily Solution

| | |
|---|---|
| 55.0 mg | 1-Methylandrosta-1,4-diene-3,17-dione |
| 55.0 mg | 11β-[(4-N,N—Dimethylamino)phenyl]17α-hydroxy-17β-(3-hydroxypropyl)-13α-methyl-4,9-gonadien-3-one |
| 343.4 mg | Castor oil |
| 608.6 mg | Benzyl benzoate |
| 1,062.0 mg | = 1 ml |

The solution is filled into an ampoule. The active agents of this invention can also be dispensed separately into two chambers with respectively one-half of the above-mentioned additives.

Pharmacological Studies

For tests on gravid guinea pigs, the antiestrogenically active compounds tamoxifen and 1-methyl-1,4-androstadiene-3,17-dione, as well as the compound showing antiprogestational activity, 11β-[(4-N,N-dimethylamino)phenyl]-17e-hydroxy-17β-(3-hydroxypropyl)-13e-methyl-4,9(10)-gonadien-3-one, were chosen as the model compounds. The dosages tested can be seen from the illustration.

Tests on Gravid Guinea Pigs

Description of Experiment

Gravid guinea pigs having a body weight of about 800 g were introduced..ed into the test on the 42nd day of pregnancy (the second day of vaginal opening in the mating phase was considered the first day of pregnancy). Prior to the beginning of the test, gravidity was checked by palpating. Treatment with the selected test compounds and, respectively, the combination took place by daily subcutaneous administration on the 43rd and 44th days of pregnancy. For this purpose, the compounds were dissolved in benzyl benzoate +castor oil (mixture ratio 2+4.5), and the daily dose in a volume of 1.0 ml was injected s.c. The possible ejection of fetuses was checked several times daily during and after treatment. On the 50th day of pregnancy, the animals were sacrificed. The uteri were inspected and the fetuses confirmed.

Results

The results of the tests regarding induction of abortion in gravid guinea pigs with combined administration of compounds having antiprogestational and anti-estrogenic activities can be seen from the illustration.

Compounds Having Anti-Estrogen Activity (AE)

At a dose of 10 mg/day s.c., 1-methyl-1,4-androstadiene-3,17-dione was totally inactive with respect to abortive effect (see illustration).

Antiprogestational Compounds (AG)

With antigestagen A, interruption of an existing pregnancy could be obtained with 10 mg/day s.c. in about 50% of the animals treated. Abortions took place with an up to 4-day latency from the beginning of treatment (see illustration).

AG/AE Combination

The combinations of antigestagen doses having merely an up to 50% efficacy (10.0 mg of A/day s.c.) with an ineffective dose of tamoxifen or 1-methyl-1,4-androstadiene-3,17-dione of 10 mg/day s.c. resulted in a 100% abortion rate and in a more rapid occurrence of abortions. The latency period in case of 1-methyl-1,4-androstadien-3,17-dione had been shortened to 0.5 day.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the induction of labor, termination of pregnancy or the treatment of gynecological disorders comprising administering to a patient in need of such an effective amount of an agent comprising at least one compound having antiprogestational activity (AG) and at least one compound having anti-estrogenic (AE) activity.

2. A method of claim 1, wherein the AG and AE are present in a weight ratio of 1:50 to 50:1.

3. A method of claim 1, wherein the AG and AE are present in a weight ratio of 1:25 to 25:1.

4. A method of claim 3, wherein the AG and AE are present in a weight ratio of 1:10 to 10:1.

5. A method of claim 1, wherein the AG and AE are present in separate dosage units.

6. A method of claim 1, wherein the AG and AE are present in a combined unit dosage.

7. A method according to claim 1, wherein the compound having antiprogestational activity is 11β-[(4-N,N-dimethylamino)phenyl]-17β-hydroxy-17α-propynyl-4,9(10)-estradien-3-one; 11β-[(4,N,N-dimethylamino)phenyl]- 17β-hydroxy-18-methyl-17α-propynyl-4,9(10)-estradien-3-one; 11β-[4,N,N-dimethylaminophenyl]-17aβ-hydroxy-17aα-propynyl-D-homo-4,9(10),16-estratrien-3-one; 11β-p-methoxyphenyl-17β-hydroxy-17α-ethynyl-4, 9(10)- estradien-3-one; 11β-(4-dimethylaminophenyl)-17α-hydroxy-17β-(3-hydroxypropyl)-13α-methyl-4,9-gonadien-3-one, or a mixture thereof.

8. A method of claim 1, wherein the compound having anti-estrogen activity is a competitive estrogen antagonist, an aromatase inhibitor, or a mixture thereof.

9. A method of claim 8, wherein the anti-estrogen is (Z)-2-[p-(1,2-diphenyl-1-butenyl)phenoxy]-N,N-dimethylethylamine;

1-[2-[4-(6-methoxy-2-phenyl-3,4-dihydro-1-naphthyl]-phenoxy]ethyl]pyrrolidine hydrochloride:

1-[p-(2-diethylaminoethoxy)phenyl]-2-(p-methoxyphenyl)-1phenylethanol:

11α-methoxy-17α-ethynyl-1,3,5(10)-estratriene-3,17β-diol: or

16β-ethylestradiol.

10. A method of claim 8, wherein the anti-estrogen is an aromatase inhibitor and is 1-methylandrosta-1,4-diene-3,17-dione;

testolactone (17a-oxa-D-homoandrosta-1,4-diene-3,17-dione);

androsta-4,6-diene-3,17-dione;

androsta-4,6-dien-17β-ol-3-one acetate;

androsta-1,4,6-triene-3,17-dione;

4-androstene-19-chloro-3,17-dione;

4-androstene-3, 6, 17-trione;

19-alkynylated steroids;

10-(1,2-propadienyl) steroids;

19-thioandrostane derivatives;

4-androsten-4-ol-3,17-dione, or one of its esters;

1-methyl-1α-alkyl-androsta-1, 4-diene-3, 17-dione;

10β-alkynyl-4,9(11)-estradiene derivatives;

1,2β-methylene-6-methylene-4-androstene-3,17-dione: or mixtures thereof.

11. A method of claim 10, wherein the amount of AE is 10–200 mg of 1-methylandrosta-1,4-diene-3,17-dione or a biologically equivalent amount of another compound having anti-estrogenic activity.

12. A method of claim 10, wherein the AE and AG are in the same dosage unit.

13. A method of claim 1, wherein the amount of AG is 1–200 mg of 11β-[(4-N,N-dimethylamino)phenyl]-17α-hydroxy-17β-(3-hydroxypropyl)-13α-methyl-4,9(10)-gonadien-3-one, or a biologically equivalent amount of another compound having antiprogestational activity.

14. A method of claim 11, wherein the amount of AE is 10–200 mg of 1-methylandrosta-1,4-diene-3,17-dione or a biologically equivalent amount of another compound having anti-estrogenic activity.

15. A method of claim 1, wherein the amount of AE is 1–100 mg of tamoxifen or a biologically equivalent amount of another compound having anti-estrogenic activity.

16. A method of claim 1, wherein the amount of AE is 10–200 mg of 1-methylandrosta-1,4-diene-3,7-dione or a biologically equivalent amount of another compound having anti-estrogenic activity.

17. A method of claim 1, wherein the treatment is for the induction of labor.

18. A method of claim 1, wherein the treatment is for the termination of pregnancy.

19. A method of claim 1, wherein the treatment is for gynecological disorders.